United States Patent [19]

Sick

[11] Patent Number: 4,500,208
[45] Date of Patent: Feb. 19, 1985

[54] APPARATUS FOR SEEKING FAULTS IN WIDE MATERIAL WEBS

[75] Inventor: Erwin Sick, Icking, Fed. Rep. of Germany

[73] Assignee: Erwin Sick GmbH Optik-Elektronik, Waldkirch, Fed. Rep. of Germany

[21] Appl. No.: 388,860

[22] Filed: Jun. 16, 1982

[30] Foreign Application Priority Data

Jun. 26, 1981 [DE] Fed. Rep. of Germany ....... 3125189

[51] Int. Cl.³ .................... G01N 21/88; G01M 11/08
[52] U.S. Cl. .................................... 356/431; 250/572
[58] Field of Search ............... 356/431, 430; 250/563, 250/572

[56] References Cited

U.S. PATENT DOCUMENTS

| 3,135,867 | 6/1964 | Daneff | 356/431 |
| 3,760,184 | 9/1973 | Brose | 356/430 |
| 4,004,153 | 1/1977 | Obser et al. | 356/430 |
| 4,260,899 | 4/1981 | Baker | 356/431 |
| 4,302,105 | 11/1981 | Sick | 250/572 |
| 4,357,071 | 11/1982 | Mankel et al. | 356/431 |
| 4,431,309 | 2/1984 | Sick et al. | 356/431 |

Primary Examiner—R. A. Rosenberger
Attorney, Agent, or Firm—Townsend and Townsend

[57] ABSTRACT

Figure 1:
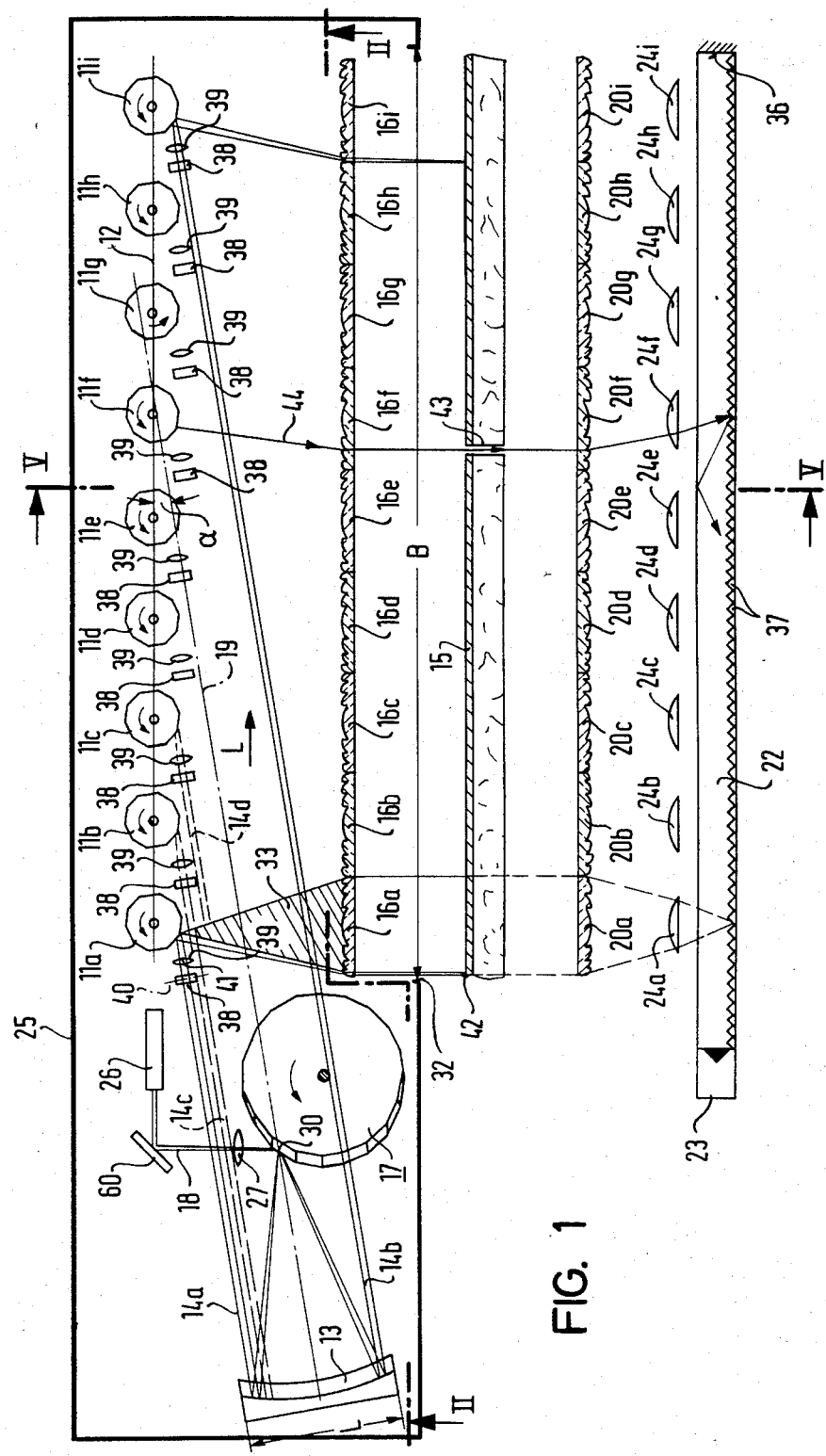

A fault seeking apparatus for detecting faults in carpet webs (15) has a first main mirror wheel (17) which is illuminated by a laser beam (18) and which generates via a concave mirror (13), a scanning beam (14) which is periodically displaced parallel to itself. This scanning beam is directed at an angle to several subsidiary mirror wheels (11a to 11i) which are arranged alongside one another, which rotate substantially faster than the main mirror wheel (17) and which generate a scanning light strip on the carpet web (15). A light receiving device consisting of lenses (20a to 20i) arranged alongside one another and a light conducting rod (22) with a photomultiplier (23) at one end face is arranged on the other side of the carpet web (15) (FIG. 1).

31 Claims, 11 Drawing Figures

APPARATUS FOR SEEKING FAULTS IN WIDE MATERIAL WEBS

The invention relates to apparatus for seeking faults in wide material webs and in particular to hole seeking apparatus for wide, moving webs of diverse material, such as paper, woven goods of all kinds, glass, laminates, wood, non-woven goods, tufted goods, sheet iron, metals, foils. Known apparatus of this kind comprises beam scanning means for scanning a sharp bead of light across the web transverse to the direction of movement to examine the web across its full width with full coverage of the scanning bead. Light receiving means including photoelectric converter means are arranged either along the web or transverse to the web to receive light transmitted and/or remitted by the web and faults in the web are detected from signals from said photoelectric converter means.

It is already known, in particular in hole seeking apparatus for wide webs such as carpets and the like which are continuously moved in their longitudinal direction, to generate a scanning beam which is continuously displaced parallel to itself and to deflect this beam towards the web at a series of stationary deflecting elements arranged one behind the other. The scanning beam is conveniently generated by means of a laser, a mirror wheel and a lens or a concave mirror. The stationary deflecting elements can either take the form of a series of laterally displaced stepped mirrors (DE-PS No. 28 08 359), or of a series of partially laterally displaced beam dividing mirrors (DE-OS No. 29 34 554).

Known hole seeking apparatus has however the disadvantage either that gaps appear in the illuminated scanned strips on the web, or that light losses occur which result in a scanning light bead with a light intensity which is too low on the web, or that high quality and accurately adjusted deflecting mirrors must be used, and/or that it is not possible to generate light scanning beams which extend along a straight line without lateral displacements.

The object of the present invention is thus to provide fault seeking apparatus for wide webs of the initially named kind by means of which a high intensity of the scanning light bead on the web is achieved without the need to use high quality deflecting mirrors, which require accurate adjustment, and without requiring displaced scanning zones. Only a single light source should, however, be required.

In order to satisfy this object the invention envisages that said beam scanning means includes a plurality of subsidiary light deflecting devices spaced apart along a line, with each subsidiary light deflecting device being arranged to scan incident light across a respective linear scanning zone on said web, and a main optical imaging element for illuminating the subsidiary light deflecting devices with light beams at an angle $\alpha$ to said line; and that said linear scanning zones jointly cover the whole width of said web.

The thought underlying the invention is thus to be seen in the fact that light deflecting devices are arranged in a row and spaced apart along a straight line with their pivot axes or axes of oscillation extending parallel to one another and at right angles to the line interconnecting them. In order to illuminate all these subsidiary light deflecting devices with light from the common main imaging element the light from the main imaging element must fall obliquely on the linear arrangement of subsidiary light deflecting devices. The smaller the angle $\alpha$ the greater is the number of subsidiary light deflecting devices arranged behind one another which can be supplied from a main imaging element without this imaging element having to be too long. For example, from five to twenty subsidiary light deflecting devices are arranged spaced apart from one another in order to embrace carpet widths of 5 m.

As the scanning light beams deflected from the subsidiary light deflecting devices all lie in one plane the subsidiary light deflecting devices cooperate to form a straight line scanning strip on the surface of the web.

The main optical imaging element is preferably a strip-like spherical concave mirror which is preferably corrected. The longitudinal direction of the strip-like concave mirror extends at right angles to the swivel or pivot axes of the subsidiary light deflecting devices. The greater the longitudinal extent of the strip-like main imaging element the greater is the number of subsidiary light deflecting devices which can be used. By using a relatively small angle $\alpha$ it is possible with a relatively short main imaging element to illuminate straightforwardly ten to twenty subsidiary light deflecting devices.

The arrangement is preferably such that the optical axis of the main optical imaging element extends at the same angle $\alpha$ to the line connecting the subsidiary light deflecting devices as the light beams which illuminate the subsidiary light deflecting devices. In other words the main optical imaging element formed by the concave mirror is preferably obliquely positioned in order to allow the light to fall obliquely on the subsidiary light deflecting devices.

An advantageous development of the invention is characterised in that the light deflecting members of the subsidiary light deflecting devices are each arranged substantially in the focal plane of a subsidiary optical imaging element, in particular a lens or a concave mirror, which makes the light coming from the associated light deflecting device substantially parallel. In this manner scanning beams which extend parallel to one another are obtained.

Neighbouring linear scanning zones should overlap by a small amount so that gaps between the individual zones are reliably avoided.

This can for example be achieved, in accordance with an advantageous further development of the invention, if the light deflecting members of the subsidiary light deflecting devices are displaced somewhat out of the focal plane of the subsidiary optical imaging elements, and if the light emerging from the subsidiary optical imaging elements is somewhat divergent so that gaps between adjacent linear scanning zones brought about by a small spacing between adjacent subsidiary optical imaging elements, or their points of contact, are avoided.

The angle between the line connecting the subsidiary light deflecting devices and the optical axis of the main imaging element should be from 1° to 5° and in particular approximately 2°.

The light deflecting members of the subsidiary light deflecting devices are expediently subsidiary mirror wheels which preferably have from five to fifteen and, in particular, approximately ten mirror surfaces.

A particularly intensive scanning light bead is obtained when the light beams are generated by a main light deflecting device which is illuminated by a light beam, in particular by a laser light beam. In this embodiment it is necessary that the scanning frequency of the main light deflecting device is at least a factor of ten and preferably a factor of 100 smaller than the scanning frequency of the subsidiary light deflecting devices. In other words, during the time in which the scanning light beam of the main light deflecting device illuminates a specific subsidiary light deflecting device the latter must complete several and preferably ten to a hundred scans so that the light beam which illuminates the subsidiary light deflecting device can be regarded as quasi stationary.

Thus, in accordance with the invention, the different subsidiary light deflecting devices are illuminated one after the other by one and the same scanning light beam. This embodiment is particularly suitable for fault seeking in carpet manufacturing machines which have an output of approximately 5 cm/sec. With machines of this kind one previously operated with two people to observe the carpet for the presence of faults. A very common fault is the absence of a thread extending in the longitudinal direction which has to be drawn through retrospectively by hand by the second man in order to repair the relevant fault after the fault has been recognised and the machine has been stopped. This method is however very costly and the quality of the result depends on the powers of observation of the people involved.

A further problem in hole recognition, particularly with tufted products, woven products or deep piled products, lies in the fact that on viewing the product at normal incidence against a light background it is possible to see very many holes ("starlit sky") which represent small faults and which are not allowed to influence the recognition of faults. In order to avoid the latter the carpet is preferably passed through the hole seeking apparatus of the invention at an angle in the order of magnitude of 45° to the scanning plane.

Furthermore it is advantageous in a carpet hole seeking apparatus if, in accordance with the invention, it is not a circular light bead that is generated on the web surface but instead a scanning light slot of up to several centimeters length. This scanning light slot should extend in the longitudinal direction of the carpet web because the threads which may be missing extend in the corresponding direction. Thus, if a thread is missing, very much more light passes through the fault to the light receiving device provided on the other side of the web. The light projected onto the web must however still be very intense because even in places where a carpet thread is missing the base fabric is still present and produces pronounced light scattering.

It is sufficient in a carpet hole seeking apparatus with a carpet advance speed of 5 cm/sec, if the main light deflecting device operates at a frequency of only 10 Hz so that it sweeps across the subsidiary light deflecting devices once every 1/10 sec. In this time the carpet web emerging from the carpet manufacturing machine advances only by an amount of 5 mm. The scanning light gap thus preferably has a length, in accordance with the invention of 30 to 60 mm and in particular approximately 50 mm. Faulty positions in the web are thus embraced by a total of ten scans of the main light deflecting device which is completely sufficient for reliable fault recognition.

The recognition on which the invention is based thus lies in the fact that for relatively slowly and continuously advanced webs one can illuminate the subsidiary light deflecting devices one after the other with a single very intensive laser beam, which expediently originates from a laser.

Thus very wide carpet webs (up to approximately 5 m) can be scanned with very intense light which originates from only a single light source. In this way light losses produced by the carrier material of the carpet (the through-illuminated fabric) are no longer so noticable that the room in which the apparatus of the invention is placed must be darkened.

If the subsidiary light deflecting devices are mirror wheels with ten mirror surfaces then the subsidiary mirror wheels rotate with a speed of approximately 6000 revolutions/min which corresponds to 1000 scans/sec.

The main light deflecting device is advantageously also a main mirror wheel which should however have more mirror surfaces than the subsidiary mirror wheels, namely, and expediently, 15 to 25 and in particular approximately 20 mirror surfaces in order to take account of the smaller scanning angle.

The main light deflecting device is preferably located in the focal plane of the main optical imaging element as is known per se in apparatus or generating a laser scanning beam which is displaced parallel to itself.

It is envisaged, in accordance with a first practical embodiment, that the light deflecting members of the subsidiary light deflecting devices are directly and obliquely illuminated by the light beams coming from the main imaging element.

In order to ensure that the light which illuminates the subsidiary light deflecting devices, in particular the subsidiary mirror wheels, falls substantially at right angles on their peripheries it is however preferable for the subsidiary light deflecting devices to comprise subsidiary light scanners and deflecting mirrors, with the deflecting mirrors being directly and obliquely illuminated by the light beams coming from the main optical imaging element and deflecting the light to the subsidiary light scanners. The arrangement should preferably be such that the line on which the deflecting mirrors are arranged extends parallel to the line on which the subsidiary light scanners are arranged. The deflecting mirrors are expediently so arranged that the light deflected from them to the subsidiary light scanners falls substantially at right angles onto the peripheries of the subsidiary light scanners.

In this manner, when using mirror wheels as the subsidiary light scanners, it is ensured that the light which illuminates the mirror wheels is incident centrally and symmetrically to their axes of rotation.

In hole seeking apparatus it is expedient if optical imaging elements, in particular lenses, are arranged alongside one another on the side of the web facing away from the subsidiary light deflecting devices.

In this connection, and in accordance with a first embodiment, photoelectric converters are arranged in the focal planes of the optical imaging elements. This construction of the light receiving means corresponds to the construction of DE-OS No. 28 08 359.

The lenses arranged in front of and behind the web are expediently Fresnel lenses the optical quality of which is completely sufficient for hole seeking purposes.

It is, however, also possible to arrange one or two preferably round light conducting rods having a photomultiplier to at least one end face in the plane of the optical imaging elements. The light conducting rod is preferably a light conducting rod with a stepped mirror arrangement on the surface side remote from the light entry side as is known for example from DE-PS No. 25 06 366.

In order to compensate for the lack of symmetry during light reception by the photomultiplier when using Fresnel lenses and/or a light conducting rod with a stepped mirror arrangement, a cylindrical lens of grey glass should be arranged between each optical imaging element and the light conducting rod. The particular advantage of the cylinder lens manufactured of grey glass resides in the fact that on grinding the lens of grey glass and increased light transmissivity is automatically achieved towards the edges and a reduced light transmissivity towards the center. The light beams impinging on the center of the filter are thus attenuated more than the side light beams. The latter are however attenuated to a greater degree by the effects of the Fresnel lenses and by the stepped mirror arrangement during further conduction inside the light conducting rod. Good directional sensitivity, and thus a reduction of the influence of stray light, can in particular be achieved by using a light receiving device comprising a cylindrical lens and a light conducting rod. In this arrangement the axis of the cylindrical lens extends parallel to the line on which the light deflecting devices are arranged and the light conducting rod is arranged behind and parallel to the cylindrical lens. The light conducting rod preferably incorporates a stepped mirror arrangement and is preferably provided with a photomultiplier at at least one end face. The directional sensitivity is improved if an arrangement of lamellae is provided in front of the cylindrical lens for light alignment.

As already mentioned above it is important that the main light deflecting device operates with a significantly lower frequency than the subsidiary light deflecting devices. The ratio of the number of scans/sec by the main light deflecting device to the number of scans per second of each subsidiary light scanning device should in particular lie between 1:50 and 1:150 and, in particular, at approximately 1:100.

Figure 2:
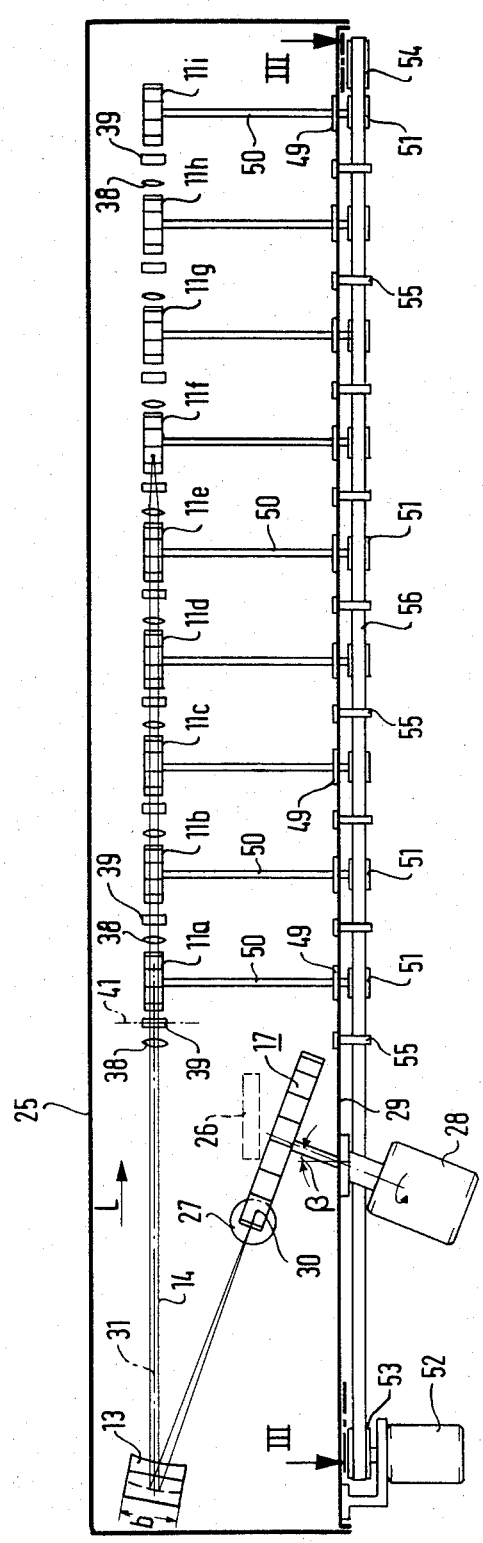
Figure 3:
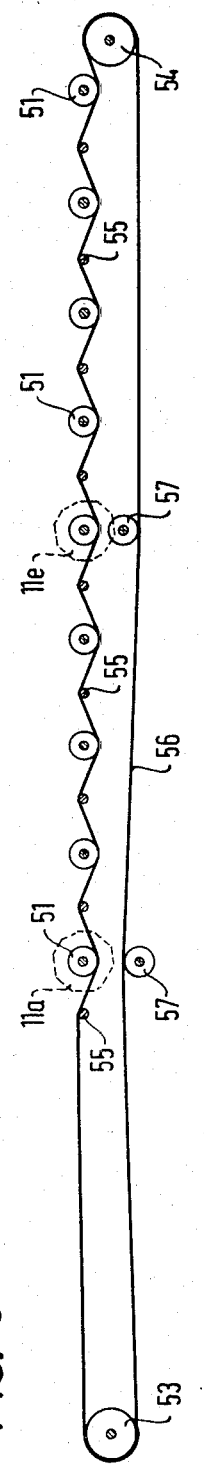
Figure 5:
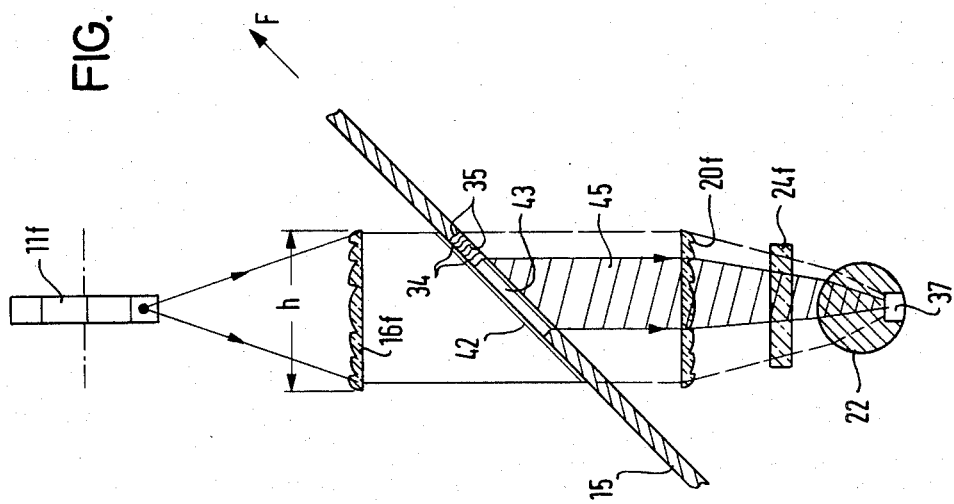
Figure 4:
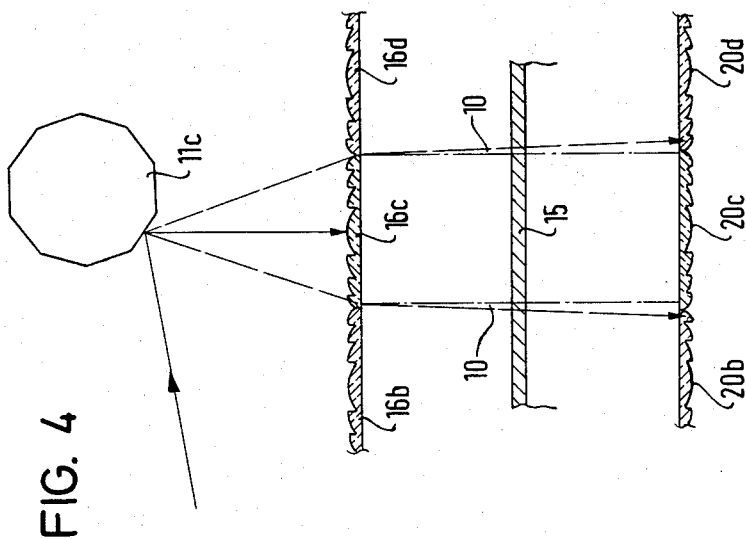
Figure 6:
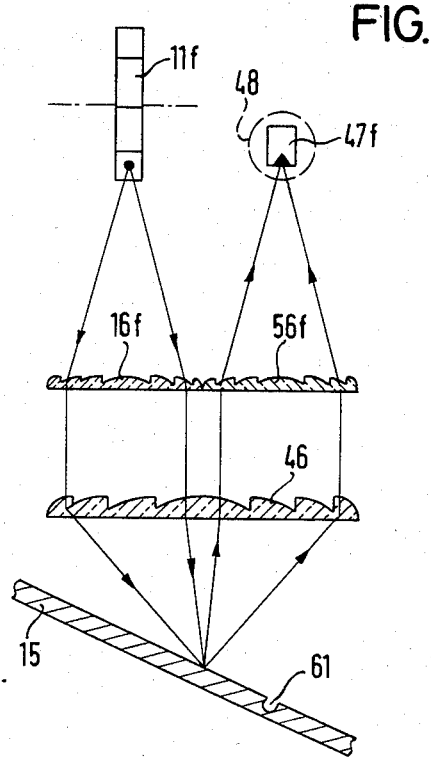
Figure 7:
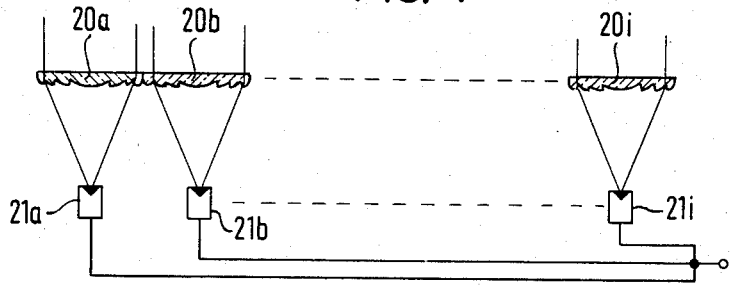
Figure 8:
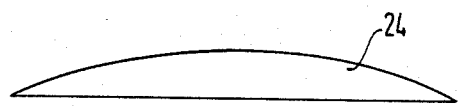
Figure 9:
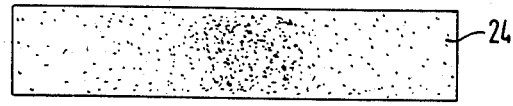
Figure 10:
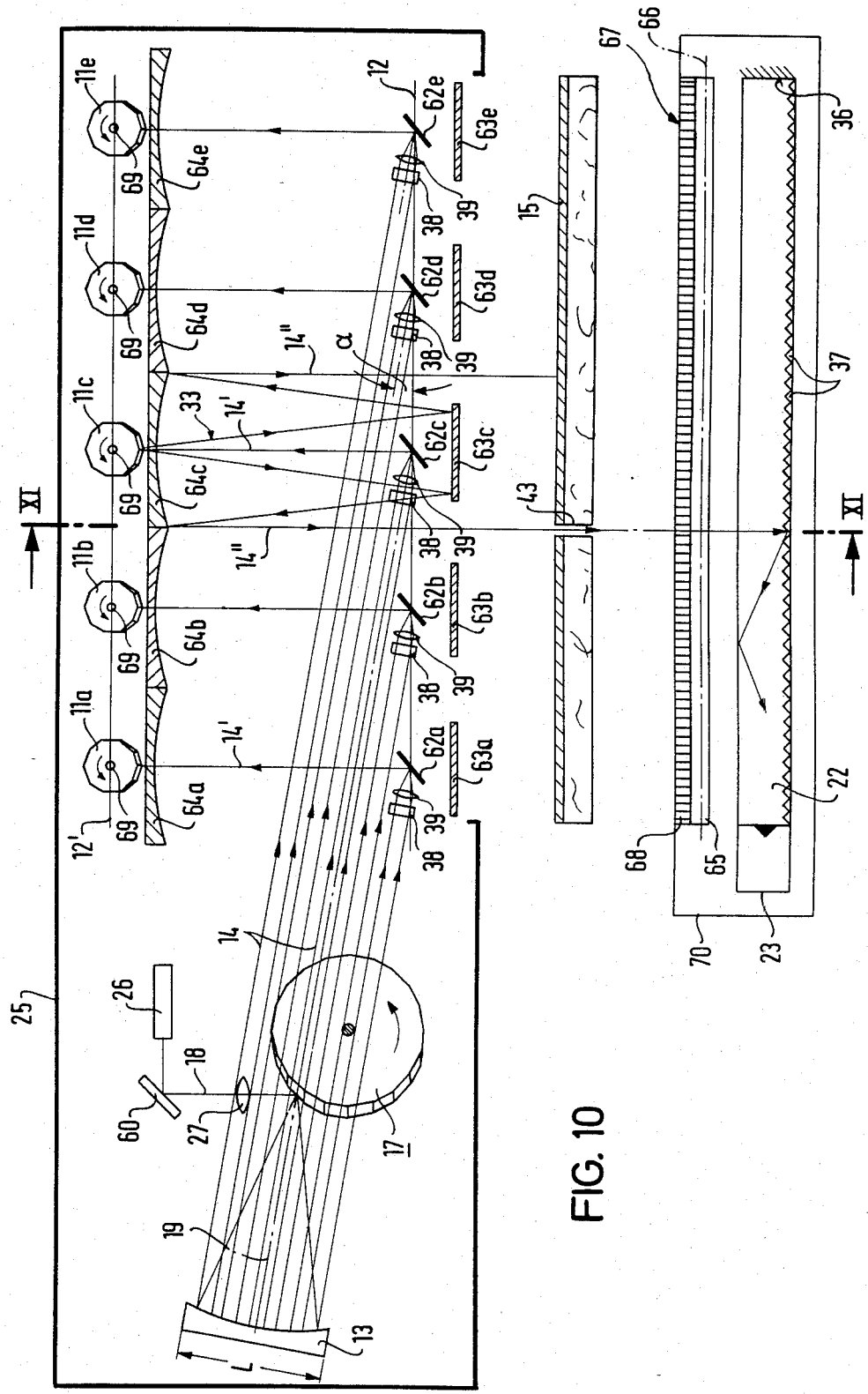
Figure 11:
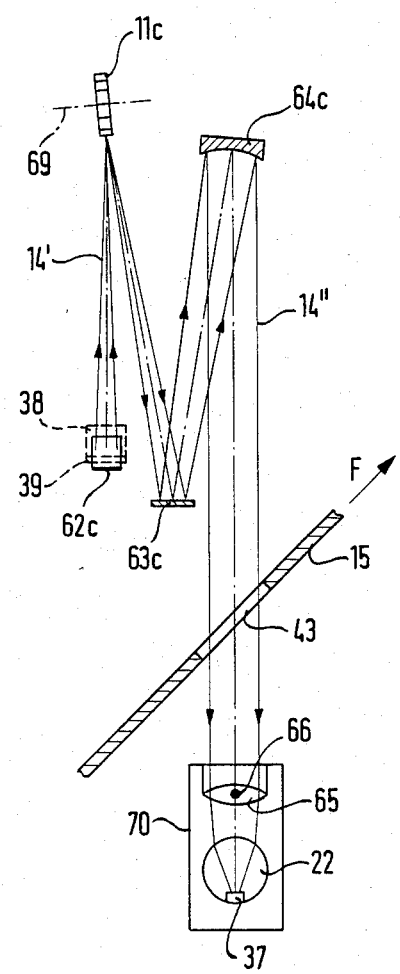

The invention will now be described in the following by way of example and with reference to the drawings which show:

FIG. 1 a schematic plan view of a hole seeking apparatus in accordance with the invention for relatively long pile carpets, FIG. 2 a partly sectioned view on the line II—II in FIG. 1, FIG. 3 a schematic plan view on the line III—III in FIG. 2 of a belt drive for subsidiary light deflecting devices in the form of mirror wheels, FIG. 4 an enlarged section of FIG. 1 in order to illustrate a detail, FIG. 5 an enlarged sectional view on the line V—V in FIG. 1, FIG. 6 a view analogous to that of FIG. 6 in a fault seeking apparatus operating in remission, FIG. 7 a light receiving apparatus operating with photoelectric converters, FIG. 8 a side view of the cylindrical lens 24 used in the embodiment of FIG. 1 but to a larger scale, FIG. 9 a plan view of the subject of FIG. 8, FIG. 10 a schematic plan view analogous to that of FIG. 1 of a further embodiment of a hole seeking apparatus in accordance with the invention, FIG. 11 a view on the line XI—XI in FIG. 10.

As seen in FIGS. 1 and 2 a laser 26 is secured in or to a housing 25, which extends transversely over a carpet web 15, in the region of one end of the longitudinal extent of the housing 25. The light beam 18 emerging from the laser 26 is concentrated via a deflecting mirror 60 and a microobjective 27, having a focal length of 50 mm for example, onto the periphery of a main mirror wheel 17. The mirror wheel 17 has twenty flat mirror surfaces on its periphery and is rotationally driven by a motor 28 (FIG. 2). The speed of rotation amounts to approximately 0.5 revolutions per second.

As can be seen from FIG. 2 in particular the axis of rotation of the mirror wheel 17 is arranged at an angle $\beta$ to the base plane 29 of the housing 25 and indeed in such a way that the laser light beam 18 of FIG. 2 which impinges on the mirror wheel 17 is reflected into a plane 31 which, when compared with the point of incidence 30 on the mirror wheel 17, lies at a larger distance from the base plane 29 so that the laser light beam can later pass by the mirror wheel 17. A strip-like spherical concave mirror 13 is arranged at a distance of approximately 500 mm from the light impingement point 30 in such a way that, as shown in FIG. 2, it reflects the incident light beam into the plane 31 along the longitudinal extent L of the housing 25. The concave mirror 13 has a focal length of 500 mm so that a parallel light beam 14 is reflected from the concave mirror 13 parallel to the optical axis 19 of the concave mirror. As the microobjective 27 is also spaced by its focal length from the point of impingement 30 the laser beam 18 is broadened by the microobjective 27 and the concave mirror 13 in the ratio 1:10. This signifies that when the light beam 18 has a diameter of 1 mm the light beam 14a transmitted from the concave mirror 13 has a diameter of 10 mm. This broadening is carried out so that the divergence of the laser scanning beam 14 which will be displaced parallel to itself on rotation of the mirror wheel 17, is held within the required limits.

In accordance with FIG. 1 the concave mirror 13 is so arranged within the housing 25 that its optical axis includes an angle $\alpha$ relative to the longitudinal extent L of the housing 25 of approximately 4° in the illustrated embodiment.

The width b of the concave mirror 13 illustrated in FIG. 2 only needs to be sufficiently large that the incident light beam is fully detected by the mirror surface even in the event of minor vibrations. The length of the concave mirror 13 which can be seen from FIG. 1 should be selected so that the two end scanning light beams 14a, 14b are spaced apart when they fall on a line 12 extending parallel to the longitudinal extent L of the housing by a distance along this line which corresponds to the width B of the carpet web 15.

The axes of equally spaced subsidiary mirror wheels 11a to 11i lie on the connecting line 12 which is arranged in the rear zone of the housing. The axes of these mirror wheels extend at right angles to the plane defined by the scanning beam 14.

The subsidiary mirror wheels 11a to 11i have only ten flat mirror surfaces at their periphery.

The spatial arrangement of the subsidiary mirror wheels 11a to 11i is, in accordance with FIGS. 1 and 2, such that the scanning light beam 14a falls at the start of its scanning movement on the first mirror wheel 11a in such a way that the scanning beam is reflected substantially at right angles to the longitudinal extent L and, on rotation of the mirror wheel 11a, in sector-like form 33 in the direction of the light exit opening 32 of the housing 25.

Whereas the main mirror wheel 17 rotates slowly so that only approximately ten scanning periods occur per second the subsidiary mirror wheels 11a to 11i rotate sufficiently fast that they sweep across the scanning sector 33 (only indicated for the subsidiary mirror wheel 11a) approximately 1000 times per second. Because of this considerable difference in scanning frequency one can regard the scanning light beams 14a in FIG. 1 as quasi-stationary.

At the end of its scanning movement the scanning light beam adopts the position 14b of FIG. 1. It now falls on the last subsidiary mirror wheel 11i.

In intermediate positions (for example 14c or 14d) the remaining subsidiary mirror wheels for example 11b, 11c are illuminated one after the other by the scanning light beam.

Directly touching Fresnel lenses 16a to 16i are provided substantially at right angles to the longitudinal extent L at a distance from the subsidiary mirror wheels 11a to 11i, with the focal points of the Fresnel lenses being located at the points of reflection on the subsidiary mirror wheels 11a to 11i. For this reason the lenses 16a to 16i render the incident light beams parallel. In this manner the light beams impinge on the surface of the carpet web 15 which, as shown in FIGS. 1 and 5, includes an angle of approximately 45° with the scanning plane of FIG. 1. For this reason it is not possible, as indicated in FIGS. 1 and 5, for the hole 35 normally present between the parts 34 of the pile to generate fault signals which is the intention because these holes, as mentioned, are normal in carpet material of this kind and are not faults.

A further arrangement of adjacent Fresnel lenses 20a to 20i is located at a distance behind the carpet web 15. A conducting rod 22 having one mirrored end face 36 and a photomultiplier which delivers the electrical output signal provided at its other end face is arranged behind and parallel to the arrangement of Fresnel lenses 20a to 20i. At its side surface opposite to the light inlet the light conducting rod 22 has a stepped mirror arrangement 37 as is known from DE-PS No. 25 08 366.

Cylindrical lenses 24a which are shown to an enlarged scale in FIGS. 8 and 9 are located between the arrangement of Fresnel lenses 20a to 20i and the light conducting rod 22. The axes of the cylindrical lenses 24a to 24i extend at right angles to the axis of the light conducting rod 22 and parallel to the mirror surfaces of the stepped mirror arrangement 37.

As seen in FIGS. 8 and 9 the cylindrical lenses 24 are of grey glass, i.e. are light absorbing to a certain degree they are however in other respects manufactured of transparent material. The initial material is uniformly absorbing at every point. As a result of the cylindrical grind shown in FIGS. 8 and 9 the transmissivity of the cylinder lens 24 changes however from the center to the edges in a reducing sense. In this way the faults produced by the Fresnel lenses 16 and 20 and by the stepped mirror arrangement 37 are automatically compensated.

As seen in FIG. 4 the Fresnel lenses 16 lie somewhat closer to the subsidiary mirror wheels 11 than the focal distance so that the emerging light beams are lightly divergent as illustrated in FIGS. 4 to 10. The angle of divergence is selected so that when a light beam enters near to the edge of the Fresnel lens 16 it does not enter the associated receiving Fresnel lens-after passing through a hole in the web 15 but instead into the neighbouring Fresnel lens (in FIG. 4 20b or 20d). In this manner gaps in scanning the carpet web 15 in the region of the contact points of the Fresnel lenses 16, 20 can be effectively avoided.

The cylindrical lenses 38 and 39 which have axes at right angles to one another and which are illustrated in FIGS. 1 and 2 are particularly important for ideal fault recognition in a hole seeking apparatus in accordance with the invention. The first cylindrical lens 38 in the beam path has an axis 40 which lies in the plane of FIG. 1, i.e. in the plane of the scanning beam 14. As illustrated in FIG. 2, at the subsidiary mirror wheel 11f, the cylindrical lens 38 initially concentrates the light beam 14 onto the mirror wheel. From the mirror wheel the emergent light beam then diverges sufficiently strongly (FIG. 5) that it illuminates the whole height h of the input Fresnel lens 16f. The axis 41 of the cylindrical lens 39 lies in the plane of FIG. 2, i.e. at right angles to the plane of FIG. 1. As illustrated in FIG. 1, at the subsidiary mirror wheel 11a, the cylindrical lens 39 ensures that the light beam 11a is concentrated at 42 onto the surface of the carpet web 15. Thus, in conjunction with the light beam broadening shown in FIG. 5, a light slot 42 is created on the surface of the carpet web 15 as schematically illustrated in FIGS. 1 and 5.

This light slot extends in the direction of movement (F in FIG. 5) of the web so that it is aligned with the faults 43 (FIGS. 1 and 5) which extend primarily in this direction.

FIGS. 1 and 5 show, by way of example, a longitudinal fault of this kind in such a way that it is detected by a light beam 44 emerging from a subsidiary mirror wheel 11f. Because of the parallelism of the gap 42 and the fault 43 a broad light band 45 now passes through the fault 43 as shown in FIG. 5 which leads to a pronounced electrical fault signal at the photomultiplier 23 (FIG. 1).

As seen in FIG. 7 a photoconverter 21a to 21i can also be arranged in the focal plane of each Fresnel lens 20a to 20i, similar to the arrangement described and shown in DE-PS No. 28 08 359. The photoconverters are connected in parallel with one another. The use of diode matrices as photoconvertors 21a to 21i is also possible. In the embodiment of FIG. 7 the grey wedge cylindrical lenses 24 are omitted.

FIG. 6 shows the application of the invention to fault recognition in remission. The web 15 can, in this arrangement, have surface faults 61 which make themselves noticable by differential remission of the incident light. In order to receive the remitted light a Fresnel lens 46 which is approximately twice as wide as the Fresnel lens 16f is arranged behind the Fresnel lens 16f and laterally displaced therefrom. The light is refracted towards the optical axis by the lens 46 and is concentrated by appropriate selection of the focal length onto the surface of the web 15. The remitted light is received by the other half of the lens 46 and is concentrated by a further Fresnel lens 56f arranged alongside the lens 16f on a photoconverter 47f of on a light conducting rod 48. The invention is thus not restricted to use for hole seeking apparatus.

As seen in FIGS. 2 and 3 the mirror wheels 11a are journalled in bearings 49 at the housing 25. Parts of the shafts 50 which extend out of the housing are provided with coaxial drive rollers 51 and a drive belt is guided over the drive rollers 51 as shown in FIGS. 2 and 3. The drive belt is driven by a drive roller 53 of a motor 52 secured at one end of the housing and is deflected into the opposite direction at the opposite end of the housing via a deflection roller 54 which is fastened to the housing. Tensioning rollers 55 are provided between the drive rollers 51 and ensure a large angle of wrap around the drive rollers 51.

The return run of the drive belt 56 from the deflection roller 54 to the drive 53 is guided over support rollers 57 to avoid fluttering.

As a result of the construction of the invention the drive belt 56 is guided alternately in the manner shown in FIG. 3 in wave-like form around a drive roller 51 and a tensioning roller 55. Thus all the subsidiary mirror wheels 11a to 11i can be jointly rotated at the same speed by a single motor 52.

In the embodiment of FIGS. 10 and 11 the same reference numerals designate parts which have counterparts in the previous embodiments.

As seen in FIG. 10 the laser 26 once again forms a light bead on the periphery of the mirror wheels 17 via the deflecting mirror 60 and the lens 27. The light beam 18 is reflected from the mirror wheel 17 to the spherical concave mirror 13. On rotation of the mirror wheel in the direction of the arrow the concave mirror 13 is thus scanned in sector-like form in the illustrated manner by the light beam 18. The concentration or parallelisation of the light beam 13 achieved by the lens 27 and the concave mirror 13 is not shown in detail in FIG. 10 because in this respect the relationships are exactly the same as in the embodiment of FIG. 1.

Thus rotation of the mirror wheel 17 creates a scanning beam 14 which extends obliquely to the longitudinal axis of the housing 25 and which is periodically displaced parallel to itself within the length L of the strip-like concave mirror 13. In order to illustrate the beam path FIG. 10 however shows the scanning beam 14 simultaneously at several different locations. In actual fact only one scanning light beam is present at any one time.

In distinction to the embodiment of FIGS. 1 and 2 the concave mirror 13 is tilted in the embodiment of FIGS. 10 and 11 directly in the opposite direction relative to the longitudinal axis of the housing 25. The concave mirror thus illuminates a line 12 extending parallel to the longitudinal axis of the housing 25 with scanning beams 14 which are located on the opposite side of the housing from the subsidiary mirror wheels 11a, which are likewise arranged on a line 12' extending parallel to the longitudinal axis of the housing 25.

Deflecting mirrors 62a, 62b, 62c, 62d, 62e are arranged in staggered form on the line 12 in such a way that the scanning light beam 14 impinges within its scanning range one after the other on the deflecting mirrors 62a to 62e. The deflecting mirrors 62a to 62e are so arranged relative to the subsidiary mirror wheels 11a to 11e that the light beans 14' reflected from the deflecting mirrors 62a to 62e to the subsidiary mirror wheels 11a to 11e extend at right angles to the longitudinal axis of the housing 25 i.e. to the lines 12, 12'. In this manner the subsidiary mirror wheels 11a to 11e are met by the light beams 14' substantially centrally and at right angles to their peripheries. In contrast to the light illuminating arrangement of FIG. 1 the mirror wheels are centrally and symmetrically illuminated and this has significant advantages with regard to the quality of optical imaging.

In order to deflect the scanning beams 14 into the direction shown in FIG. 10 at right angles to the longitudinal axis of the housing the deflecting mirrors 62a to 62e must be arranged at angles to to the longitudinal axis of the housing 25 or to the line 12 which are somewhat less than 45°. The angle α at which the light beams 14 illuminate the line 12 is substantially the same as that in the embodiment of FIGS. 1 and 2.

In distinction to the embodiment of FIGS. 1 and 2 the subsidiary mirror wheels 11a to 11e of FIGS. 10 and 11 generate the subsidiary scanning beams which are displaced parallel to themselves, not by means of Fresnel lenses but instead by means of spherical concave mirrors 64a, 64b, 64c, 64d, 64e.

The generation of subsidiary scanning beams 14″ by the subsidiary mirror wheel 11c is illustrated in FIGS. 10 and 11. The generation of the subsidiary scanning beams by the remaining subsidiary mirror wheels takes place in analogous manner.

As seen in FIGS. 10 and 11 the rotational axes 69 of the subsidiary mirror wheels 11c are fractionally inclined in such a way that the light 14' reflected from the deflecting mirrors 62a to 62e is reflected by the mirror wheels 11a to 11e into a plane above the deflecting mirrors 62a to 62e. This can be seen particularly clearly from FIG. 11. Strip-like plane mirrors 63a to 63e which extend parallel to the longitudinal axis of the housing 25, i.e. to the line 12 and are spaced from the associated subsidiary mirror wheels 11a to 11e are located in the zone above the deflecting mirrors 62a to 62e. As, on rotation of the subsidiary mirror wheels 11a to 11e, the light beams 14' are reflected within a scanning sector 33 the mirrors 63a to 63e must have a length such that all reflected light beams fall within the scanning sector 33.

Spherical concave mirrors 64a to 64e which receive light reflected from the strip-like plane mirrors 63a to 63e are located closely alongside one another in the region above the subsidiary mirror wheels 11a to 11e. The arrangement and construction of the mirror wheels 11a to 11e is such that the light beams deflected within the scanning sector 33 sweep completely across the individual strip-like spherical concave mirrors 64a to 64e. The concave mirrors lie directly alongside one another so that the subsidiary scanning beams 14″ of neighbouring concave mirrors border on one another and a continuous scanned zone is obtained on the web.

The subsidiary mirror wheels 11a to 11e are arranged somewhat inside the focal length of the concave mirrors, taking account of the beam deflection by the strip-like plane mirrors 63a to 63e, so that generally diverging subsidiary scanning beams 14″ are obtained and no gaps occur between neighbouring subsidiary scanning arrangements.

In analogy to the embodiment of FIGS. 1 and 2 the subsidiary scanning beams 14″ once again sweep across the web 15 which is to be examined for faults. FIG. 10 shows a subsidiary scanning beam 14″ which is just passing through a fault 43 in the carpet web 15.

It can be seen from FIG. 11, which is a view analogous to that of FIG. 5, that in this embodiment also the carpet web 15 extends at an angle to the incident scanning beams. The web is moved in the direction of the arrow F.

A receiving device 70 is provided at the side remote from the subsidiary mirror wheels 11a to 11e. In the present embodiment the receiving device 70 has a cylindrical lens 65 which extends across the scanning zone and a light conducting rod 22, with a stepped mirror arrangement 37 at its side surface opposite to the light inlet, arranged behind the cylindrical lens. The arrangement is such that only parallel light entering into the cylindrical lens 65 is concentrated onto the stepped mirror arrangement 37 so that a certain directional selectivity is obtained and stray light can hardly disturb the receiving arrangement.

The axis 66 of the cylindrical lens 65 extends parallel to the lines 12, 12' in the receiving part. The light conducting rod 22 is in turn arranged parallel to the axis 66 of the cylindrical lens 65. A photomultiplier is located at one end of the light conducting rod whereas the opposing end face is mirrored at 36.

In order to further improve the directional action of the receiving arrangement 70 an arrangement of lamellae consisting of closely spaced mat black walls 68 extending vertically and parallel to the incident subsidiary scanning beam 14'' provided in front of the cylindrical lens 65. In this manner stray light incident obliquely on the arrangement of lamella 67 cannot reach the cylindrical lens 65 and can therefore also not reach the light conducting rod 22 and the photomultiplier 23.

The advantage of using concave mirrors 64a to 64e in comparison with Fresnel lenses lies in the fact that the aperture ratio of the concave mirrors can be substantially larger. Whereas Fresnel lenses can generally only have a length of 65 cm it is straightforwardly possible to provide the strip-like concave mirrors 64a to 64e with a length of 50 cm. Thus for the same scanning lenth one only requires half the number of subsidiary light deflecting devices. In this way the complexity involved in obtaining a scanning length of, for example, 5 m can be significantly reduced.

It should be particularly emphasised that in the fault seeking apparatus of the invention only a single laser is required for all the subsidiary light deflecting devices and for the whole of the extremely wide scanning beam. Moreover, it should be emphasised that only a single drive motor, if necessary with a gearbox, need be provided for the numerous subsidiary light deflecting devices in particular the mirror wheels.

It should once again be emphasised that the angle α should be made sufficiently large that the light beam coming from the mirror wheel and moved parallel to itself does not hinder the next light beam during its transition from one deflecting mirror to the next.

The material guiding means can advantageously also be tiltable and/or adjustable so that the angle at which the light falls on the transversely scanned material web can be ideally adjusted to the material that is used.

In FIGS. 1 and 10 a substantially smaller angle of tilt of the web 15 is assumed than in FIG. 5, i.e. the web 15 lies at a steeper angle relative to the drawing in FIGS. 1 and 10.

I claim:

1. Apparatus for seeking faults in wide material webs during movement of the same, the apparatus comprising:
   beam scanning means for scanning a sharp light beam across the web transverse to the direction of web movement to examine the web across its full width with full coverage of the scanning beam;
   light receiving means including photoelectric converter means arranged along the web to receive the light beam from the web according to the presence of a fault in the web, whereby faults in the web are detected from signals from said photoelectric converter means;
   said beam scanning means including a main light deflecting device, illuminated by the light beam, for sequentially scanning a plurality of subsidiary light deflecting devices spaced apart along a first line with each subsidiary light deflecting device being arranged to scan the light beam incident thereon across a respective linear scanning zone on the web; and
   a main optical imaging element for successively illuminating the subsidiary light deflecting devices with the light beam at an angle to said first line, said linear scanning zones jointly covering the full width of the web.

2. The apparatus of claim 1 wherein the subsidiary light deflecting devices include subsidiary light scanners which are each arranged substantially in the focal plane of a subsidiary optical imaging element so light coming from the associated subsidiary light scanners is substantially parallel.

3. The apparatus of claim 2 wherein the subsidiary light deflecting devices are displaced somewhat out of the focal plane of the subsidiary optical imaging elements so light emerging from the subsidiary optical imaging elements is somewhat divergent to eliminate gaps between adjacent linear scanning zones.

4. The apparatus of claim 2 further comprising:
   deflecting mirrors each positioned to deflect light along a first path from the main optical imaging element to a light reflecting surface of the subsidiary light deflecting device;
   the subsidiary optical imaging elements arranged to deflect light from the first path to a second path at a second angle to the first path;
   strip-like plane mirrors each positioned along the second path to one side of the deflecting mirrors to reflect light from the second path to a third path; and
   concave mirrors placed along said third paths, each concave mirror positioned to reflect light from the third path to a fourth path and toward the web, the focal points of each of the concave mirrors lying in the region of the light reflecting surfaces of the subsidiary light deflecting devices.

5. The apparatus of claim 4 wherein the surface of each of the subsidiary light deflecting devices lies so far inside the focal length of the concave mirrors that light along the third path diverges slightly.

6. The apparatus of claim 1 wherein neighboring linear scanning zones overlap by a small amount.

7. The apparatus of claim 1 wherein said angle is from 1° to 5°.

8. The apparatus of claim 7 wherein the angle is about 2°.

9. The apparaus of claim 1 wherein the subsidiary light deflecting devices include subsidiary mirror wheels.

10. The apparatus of claim 9 wherein the subsidiary mirror wheels have from five to fifteen mirror surfaces.

11. The apparatus of claim 10 wherein the subsidiary mirror wheels have about ten mirror surfaces.

12. The apparatus of claim 1 wherein the main light deflecting device includes a main mirror wheel.

13. The apparatus of claim 12 wherein the main mirror wheel has from fifteen to twenty-five mirror surfaces.

14. The apparatus of claim 15 wherein said main mirror wheel has about 20 mirror surfaces.

15. The apparatus of claim 1 wherein the main optical imaging element includes a spherical, gathering optical element and the main light deflecting device is located in the focal plane of said spherical, gathering optical imaging element.

16. The apparatus of claim 1 wherein the main optical imaging element has an optical axis which extends at said angle to said first line.

17. The apparatus of claim 1 wherein the subsidiary light deflecting devices are directly and obliquely illuminated by the light beam coming from the main optical imaging element.

18. The apparatus of claim 1 wherein the subsidiary light deflecting device comprise subsidiary light scanners and deflecting mirrors with the deflecting mirrors being directly and obliquely illuminated by the light beam coming from the main optical imaging element and deflecting the light beam to the subsidiary light scanners.

19. The apparatus of claim 18 wherein the deflecting mirrors are arranged on a second line which extends parallel to a third line on which the subsidiary light scanners are arranged.

20. The apparatus of claim 18 wherein the deflecting mirrors are so arranged that light deflected from them to the subsidiary light scanners falls substantially at right angles onto the subsidiary light scanners.

21. The apparatus of claim 1 further comprising optical image forming elements, having focal planes, arranged alongside one another on a side of the web facing away from the subsidiary light deflecting devices.

22. The apparatus of claim 21 wherein said optical image forming elements include lenses.

23. The apparatus of claim 21 wherein the photoelectric converter means is arranged in the focal planes of the optical image forming elements.

24. The apparatus of claim 21 wherein the optical image forming elements define a common focal plane, extending parallel to said first line, and wherein the photoelectric converter means includes a light conducting rod, having a rod axis, with a photomultiplier at at least one end face, said light conducting rod arranged in said common focal plane.

25. The apparatus of claim 21 wherein the light conducting rod has a light inlet at one side and a stepped mirror arrangement at another side opposite the light inlet, and further comprising a cylindrical lens of gray glass arranged between each optical image forming element and the light conducting rod, each said gray glass lens having a lens axis extending at a right angle to the rod axis.

26. The apparatus of claim 1 wherein said light receiving means includes:
a cylindrical lens having a cylindrical lens axis extending parallel to said first line; and
a light conducting rod arranged behind and parallel to the cylindrical lens and having a stepped mirror arrangement along one side and a photomultiplier at at least one end face thereof.

27. The apparatus of claim 26 further comprising an arrangement of lamellae provided in front of the cylindrical lens for light alignment.

28. The apparatus of claim 1 wherein the ratio of the number of scans per second by the main light deflecting device to the number of scans per second of each of the subsidiary light deflecting devices line between 1:50 and 1:150.

29. The apparatus of claim 28 wherein said scan ratio is about 1:100.

30. The apparatus of claim 1 wherein the web is at an angle of about 45° to the light beam impinging thereon.

31. The apparatus of claim 1 further comprising a common drive for all said subsidiary light deflecting devices.

* * * * *